United States Patent [19]

Tenta

[11] 3,949,072

[45] *Apr. 6, 1976

[54] TOPICAL COMPOSITION FOR TREATMENT OF SEBORRHEIC KERATOSIS

[76] Inventor: Louis T. Tenta, 6007 N. Sheridan Road, Chicago, Ill. 60660

[ * ] Notice: The portion of the term of this patent subsequent to June 28, 1991, has been disclaimed.

[22] Filed: May 1, 1974

[21] Appl. No.: 465,740

Related U.S. Application Data

[63] Continuation-in-part of Ser. No. 123,380, March 11, 1971, Pat. No. 3,821,370.

[52] U.S. Cl. ............... 424/145; 424/235; 424/343; 424/DIG. 13
[51] Int. Cl.$^2$ ........................................ A61K 33/30
[58] Field of Search ................. 424/145, 235, 343

[56] References Cited
UNITED STATES PATENTS 3,317,382   5/1967   Brunner et al. .............. 424/DIG. 13
3,821,370   6/1974   Tenta ................................ 424/343

OTHER PUBLICATIONS

Chemical Abstracts, Vol. 73 (1970), p. 85, 963W.
Gregory, "Uses & App. of Chem. & Related Materials", (1939), pp. 16, 504, 551, 554, 648, Reinhold Pub. Co.

*Primary Examiner*—V. D. Turner
*Attorney, Agent, or Firm*—Hill, Gross, Simpson, Van Santen, Steadman, Chiara & Simpson

[57]   ABSTRACT

An improved topical composition for application to skin effected by seborrheic keratosis so as to provide a superficial slough of the epidermis, the composition containing an inhibited phenol, preferably potassium phenolate, a salicylate, a zinc compound and resorcinol, the active ingredients being dissolved in a non-aqueous solvent which includes a hydrophilic nontoxic lower aliphatic alcohol, the amount of phenolate present being generally lower than the amount of phenolate in comparable compositions.

10 Claims, No Drawings

3,949,072

TOPICAL COMPOSITION FOR TREATMENT OF SEBORRHEIC KERATOSIS

REFERENCE TO RELATED APPLICATION

This application is a continuation-in-part of my copending Ser. No. 123,380 filed Mar. 11, 1971 now U.S. Pat. No. 3,821,370.

BACKGROUND OF THE INVENTION

1. Field of the Invention

This invention is in the field of topical compositions for the treatment of seborrheic keratosis and includes as its essential ingredients, inhibited phenol, a salicylate, resorcinol, a zinc compound, and a non-aqueous solvent including a non-toxic lower aliphatic alcohol.

2. Description of the Prior Art

In my copending application, now U.S. Pat. No. 3,821,370, I have described a topical composition for use in the treatment of various skin conditions, including seborrheic keratosis. In this patent, there was suggested a composition containing 20 to 60 parts of an inhibited phenol calculated as potassium phenolate, 1 part of a salicylate calculated as sodium salicylate, 5 parts of resorcinol, and 4 parts of a zinc compound calculated as zinc sulfate. The present invention provides a significant improvement over the type of compositions disclosed in the aforementioned patent by reducing the amount of inhibited phenol required to produce the same ameliorative effect.

SUMMARY OF THE INVENTION

The present invention relates to a topical composition for application to the skin to improve the external appearance that may be caused by certain skin disorders. In order to understand more clearly the action of my topical composition upon its application to the skin for the general purpose just stated, the following background information might be helpful.

The skin is composed of two layers, a thin, outer layer, the epidermis, which is about 0.1 mm. in thickness and a deeper, thicker layer, the dermis, of up to 2 to 4 mm. in thickness, depending upon its location in the human body.

The epidermis is composed of cells arranged in layers, with the outermost layer cells thickened or, as it is sometimes known, keratinized or hornified. Pigment cells are present in the deepest layer as well as in the "parent" cells which give rise to generations of younger cells to replace those lost to attrition and to wear and tear.

The dermis contains blood vessels and nerves which provide nutrition and sensation, respectively. Moreover, there are lymphatic vessels present which might be thought of as conveying "tissue juices". Additionally, the structures from which hairs grow (follicles) and glands which lubricate the skin are contained in the dermis. From these structures project small tubes or channels which penetrate the epidermis and open upon the surface of the skin in the form of hairs and/or pores. These structures of the dermis (vessels, nerves, follicles and glands) are surrounded by cells which are referred to as connective tissue cells. These cells may be considered as a support or superstructure for the overlying epidermis as well as supporting the vessels, nerves, follicles and glands within the dermis proper.

Moreover, intertwined among these various cells and structures contained within the dermis are elastic threads or fibers which permit the skin to regain shape after stretching. Additionally, the connective tissue cells are involved in the repair of these tissues from injurious or noxious sources. The repaired area of the tissue is manifested as a scar.

Many disorders may affect the skin. Some are a consequence of a local effect (such as a laceration, or cut) while others may reflect underlying constitutional disorders (such as the yellowing of skin that may occur in liver diseases).

Of those disorders that might be considered as arising from disturbances that are local in nature, certain ones will now be selectively discussed. Various changes occur which may affect the structure of anatomy of the skin. These changes may be manifested as a thickening of the outermost (keratinized or hornified) layer of the epidermis, and the resulting formation of brown or beige-colored warty-like areas (seborrheic keratosis). A change in the pigmentation of the skin may occur which produces random areas of brownish or tan discoloration. Moreover, unsightly scarring may occur as a consequence of acne eruptions or from superficial burns. A loss of the elastic fibers necessary for normal skin consistency may result from the stretch marks of obesity or pregnancy or from the effects of wasting scars.

Additionally, certain types of "birth marks" (which usually result from abnormally formed and expanded blood vessels) affect the color of the skin. Aging alters the skin structure by causing a weakness of the elastic fibers which results in a relaxation of the skin and consequent wrinkling. The objectionable external appearance caused by these disorders may be minimized or corrected in a non-surgical fashion by the application of a composition, such as that disclosed herein, which is not harmful to one's health and which produces two fundamental and simultaneous reactions, one in the epidermis and another in the dermis.

These reactions occur at the site of the basic disorder and produce two responses, the one response being that of a superficial slough of the epidermis; and the other response being a stimulation of the connective tissue cells in the dermis. These responses, in turn, are manifest by a peeling of the outermost skin layer and the consequent removal of surface irregularities, blemishes and discolorations, and by a strengthening of the underlying dermis which results from an increase in the numbers of connective tissue cells which surround and support the hair follicles, glands and vessels. This produces a firmer and more consistent support for the skin, which is manifest by a minimizing of depressions, wrinkles and scars. Moreover, this same response may cause the obliteration or collapse of certain poorly formed blood vessels in the dermis and result in the disappearance or fading of certain types of birth marks.

The composition of the present invention includes phenol in an inhibited form which is rendered active by exposure to the moisture in the air or the moisture from the skin. To accelerate this response, I include in the new composition a non-aqueous solvent which includes a hydrophilic lower aliphatic (2 to 4 carbon atoms) non-toxic alcohol. The alcohol apparently absorbs significant amounts of moisture and initiates the reaction on the skin which is characterized by warmth and redness, or blushing of the skin. This response is followed quickly in turn by a frosting of the skin and a sensation of tautness or tightening. These reactions occur within minutes after the application of the composition has been applied. Over the next three to five days, the skin takes on the character of an onion skin, somewhat rusty or violaceous in color, following which a flaking or peeling occurs which exposes from beneath a clearer, cleaner, smoother appearing surface.

The inhibited phenol of the present invention may be either potassium phenate, sodium phenate or ammonium phenate. These phenates can be produced by neutralizing 90% phenol with the corresponding alkali metal or ammonium hydroxide. The product is then recovered by crystallization with ether.

DESCRIPTION OF THE PREFERRED EMBODIMENTS

The topical composition of the present invention includes, as its active ingredients, from 5 to 25 parts by weight of an inhibited phenol, calculated as potassium phenate, ½ to 2 parts of a salicylate calculated as sodium salicylate, 1 to 5 parts of resorcinol, 1 to 4 parts of a zinc compound calculated as zinc sulfate, and a non-aqueous solvent system including a hydrophilic non-toxic lower aliphatic alcohol (2 to 4 carbon atoms) in an amount sufficient to bring the total to 100 parts by weight. As previously noted, the inhibited phenol may be potassium phenate, sodium phenate or ammonium phenate. A particularly preferred concentration of the phenate is from 10 to 20 parts by weight and, even more preferred is a concentration of about 18 to 19 parts by weight calculated as potassium phenate. In this connection, potassium phenate contains approximately 70% by weight of equivalent phenol.

The salicylate may be sodium salicylate or zinc salicylate. The use of zinc in any available form, such as zinc oxide, zinc sulfate, or other zinc compounds, including zinc salicylate is believed to enhance and augment the subepithelial changes without necessitating any increase in the resorcinol and/or phenol concentrations to such a level that irreparable chemical destruction of the epithelium and subepithelial structures may occur.

The compositions of the present invention can be used as solutions because of their stability, their relative non-volatility, and the absence of precipitation of the active ingredients. The solvent system employed in the present invention includes a hydrophilic, nontoxic aliphatic alcohol. It is not practical to use a 95% alcohol solution so I prefer to use solvent systems which include other non-toxic solvents which, when combined with the alcohol, provide a solution with greater viscosity and less volatility than would be characteristic of an alcohol solution. Specifically, I prefer to use a solvent system containing about 61.5% weight benzyl alcohol and 38.5% ethanol. Another satisfactory system contains 50% by weight propylene glycol and 50% by weight ethanol.

In addition to their use as true solutions, the compositions of the present invention can be employed in gel form. Any non-toxic gel forming agent can be used for this purpose, and hydroxyethylcellulose is particularly preferred. A sufficient amount of the gelling agent is added to the solution of active ingredients until a gel of the desired viscosity is obtained. The amount of gelling agent will depend upon the concentration of the active materials, particularly the phenates, as well as viscosity requirements, mixing speeds, pressure conditions, temperature, anerobic environment, and other physical characteristics.

The non-aqueous solutions or gels of the present invention are more stable, uniform and clinically active at lower concentrations of the active ingredients than similar compositions of the past.

Representative examples of solutions produced according to the present invention are given below:

EXAMPLE 1

| | | |
|---|---|---|
| Potassium phenate | 21 | % by weight |
| Resorcinol | 1 | " |
| Anhydrous zinc sulfate | 1 | " |
| Sodium salicylate | 1 | " |
| Benzyl alcohol | 46 | " |
| Ethanol | 30 | " |

EXAMPLE 2

| | | |
|---|---|---|
| Potassium phenate | 14 | % by weight |
| Resorcinol | 2 | " |
| Anhydrous zinc sulfate | 1 | " |
| Sodium salicylate | 2 | " |
| Benzyl alcohol | 51 | " |
| Ethanol | 30 | " |

EXAMPLE 3

| | | |
|---|---|---|
| Potassium phenate | 7 | % by weight |
| Resorcinol | 2 | " |
| Zinc salicylate | 4 | " |
| Zinc oxide | 1 | " |
| Benzyl alcohol | 52 | " |
| Ethanol | 34 | " |

EXAMPLE 4

| | | |
|---|---|---|
| Potassium phenate | 21 | % by weight |
| Resorcinol | 1 | " |
| Anhydrous zinc sulfate | 1 | " |
| Sodium salicylate | 1 | " |
| Propylene glycol | 38 | " |
| Ethanol | 38 | " |

EXAMPLE 5

| | | |
|---|---|---|
| Potassium phenate | 14 | % by weight |
| Resorcinol | 2 | " |
| Anhydrous zinc sulfate | 1 | " |
| Sodium salicylate | 1 | " |
| Propylene glycol | 41 | " |
| Ethanol | 41 | " |

EXAMPLE 6

| | | |
|---|---|---|
| Potassium phenate | 7 | % by weight |
| Resorcinol | 2 | " |
| Zinc salicylate | 1 | " |
| Zinc oxide | 1 | " |
| Propylene glycol | 44.5 | " |
| Ethanol | 44.5 | " |

The solutions of Examples 1 to 6 can be made into stable gels to the addition of suitable gelling agents such as cellulosic derivatives. Hydroxyethylcellose is particularly preferred but other binders such as carboxymethyl cellulose can also be employed. Each of the solutions of Examples 1 to 6 can be made into a stable gel by the addition of about 5 to 15% by weight of the cellulose derivative.

The non-aqueous solutions or gels of the present invention are more stable, uniform and clinically active at lower concentrations of the active ingredients than in previous systems. Consequently, the lower resultant concentration of potassium phenate permits the application of these compositions in either solution or gel form in proportions that cover a larger area of skin. For example, a solution containing 1 gram of potassium phenate in the improved formulation of the present invention can be used to treat approximately 200 square centimeters of skin.

It should be evident that various modifications can be made to the described embodiments without departing from the scope of the present invention.

I claim as my invention:

1. A topical composition for application to skin affected by seborrheic keratosis to provide a superficial slough of the epidermis, said composition comprising from 5 to 25 parts by weight of an inhibited phenol calculated as potassium phenate and selected from the group consisting of potassium, sodium and ammonium salts of phenol; one-half to two parts of a salicylate calculated as sodium salicylate and selected from the group consisting of sodium and zinc salicylate; 1 to 5 parts of resorcinol; and 1 to 4 parts of a zinc compound calculated as zinc sulfate selected from the group consisting of zinc salicylate, zinc oxide, and zinc sulfate, the aforementioned inhibited phenol, salicylate, and zinc compound being dissolved in a non-aqueous solvent containing a hydrophilic non-toxic lower aliphatic alochol in an amount sufficient to bring the total to 100 parts by weight said non-aqueous solvent being sufficient to increase the viscosity and to reduce the volatility of the resultant composition.

2. The topical composition of claim 1 in which said lower aliphatic alcohol is ethanol.

3. The topical composition of claim 1 in which said solvent consists of a mixture of benzyl alcohol and ethanol.

4. The topical composition of claim 1 in which said solvent consists of a mixture of propylene glycol and ethanol.

5. The topical composition of claim 1 which also contains sufficient amount of a gel forming agent selected from the group consisting of hydroxyethylcellulose and carboxymethylcellulose, to form a stable gel.

6. The composition of claim 5 in which the gel forming agent is hydroxyethylcellulose.

7. The composition of claim 1 in which the concentration of the inhibited phenol is in the range from 10 to 20 parts by weight.

8. The composition of claim 1 in which said salt is potassium phenate and said phenate constitutes from 5 to 25% by weight of the composition.

9. The composition of claim 8 in which said phenate constitutes from 10 to 20% by weight of the composition.

10. A method for treating an effected skin area to minimize the objectionable appearance of seborrheic keratosis thereon which comprises applying to the affected skin area the composition of claim 1, said composition being applied to the skin in an amount equivalent to one gram of potassium phenate per 200 square centimeters of skin area.

* * * * *